United States Patent [19]

Acosta et al.

[11] Patent Number: 5,772,627
[45] Date of Patent: Jun. 30, 1998

[54] ULTRASONIC TISSUE RESECTOR FOR NEUROSURGERY

[75] Inventors: George M. Acosta, Long Beach; Derek J. Daw, Costa Mesa, both of Calif.

[73] Assignee: Neuro Navigational Corp., Costa Mesa, Calif.

[21] Appl. No.: 684,425

[22] Filed: Jul. 19, 1996

[51] Int. Cl.⁶ .................................................. A61B 17/20
[52] U.S. Cl. ............................ 604/22; 606/169; 606/128
[58] Field of Search ............................ 601/2, 3; 604/22; 606/169, 128; 128/898

[56] References Cited

U.S. PATENT DOCUMENTS

| | | | |
|---|---|---|---|
| 4,869,715 | 9/1989 | Sherburne | 604/22 |
| 4,923,441 | 5/1990 | Shuler | 604/22 |
| 5,061,238 | 10/1991 | Shuler | 604/22 |
| 5,318,526 | 6/1994 | Cohen | 604/95 |
| 5,324,255 | 6/1994 | Passafaro et al. | 604/22 |
| 5,324,297 | 6/1994 | Hood et al. | 606/99 |
| 5,359,996 | 11/1994 | Hood | 604/22 |
| 5,382,228 | 1/1995 | Nita et al. | 604/22 |

*Primary Examiner*—Aaron J. Lewis
*Assistant Examiner*—Kelly O'Hara
*Attorney, Agent, or Firm*—John L. Rogitz

[57] ABSTRACT

An ultrasonic tissue resector is slidably engaged with a working channel of a flexible neuroendoscope for resecting brain tumors, cysts, hematomas, and herniated spinal discs. The resector includes a piezoelectric transducer for generating ultrasonic energy. The ultrasonic energy is coupled to an ultrasonic probe having a rigid proximal segment for transmitting the energy therealong and a flexible distal segment which can bend to conform to the flexible neuroendoscope. An aspiration channel is provided, and the resector can be endoscopically positioned in the brain through the neuroendoscope and energized to ultrasonically break up tissue such as tumors, cysts, and hematomas and remove the tissue through the aspiration channel.

8 Claims, 4 Drawing Sheets

ULTRASONIC TISSUE RESECTOR FOR NEUROSURGERY

FIELD OF THE INVENTION

The present invention relates generally to neurosurgery, and more particularly to methods and apparatus for removing diseased neurological tissue, such as spinal discs, using ultrasound.

BACKGROUND

Brain tumors, cysts, and neural hematomas pose severe health risks to patients who are afflicted by them. Depending upon the particular circumstances, one treatment is to resect, i.e., to break up and remove, the tumor, cyst, or hematoma from the neurologic system of the patient. For purposes of the present invention, the neurologic system includes the brain and spinal cord.

It will be appreciated that the resection of, e.g., a brain tumor, must be precisely accomplished, to avoid damaging healthy brain tissue nearby the tumor. Even slight damage to healthy brain tissue can have grave consequences for the patient. Likewise, it is sometimes necessary to remove a herniated spinal disc, and it is important not to damage healthy spinal cord tissue nearby the disc. Accordingly, the present invention recognizes the need to provide a tissue resector which can be precisely controlled and which advantageously can be used in less invasive neurosurgery, i.e., in conjunction with a neuroendoscope, to minimize the risk of damaging healthy brain or spinal tissue and to minimize patient trauma.

As further recognized by the present invention, ultrasonic energy from an ultrasonic probe can be precisely controlled and applied to tissue to break up the tissue. Typically, such a probe is caused to vibrate very rapidly (in the kiloHertz range) in the longitudinal dimension of the probe, and when the probe tip is positioned near tissue, the longitudinal vibrations of the probe generate cavitation in or near the tissue to break up the tissue.

The source of the vibrations in ultrasonic probes is usually either a piezoelectric crystal transducer or a magnetostrictive device which mechanically vibrates when energized with electrical current, and the transducer is coupled to the probe to transmit the vibrations of the transducer to the tip. The movement caused by the ultrasonic energy generated by the crystal transducer can be advantageously amplified by coupling the crystal to one or more rigid amplifiers, such as, e.g., a so-called "horn". As disclosed in U.S. Pat. No. 5,269,297, a horn is a structure that has a longitudinal length of an integer multiple of one-half of the ultrasound wavelength.

Desirably, to optimize the performance of the probe and facilitate application of energy to the target tissue, which might be accessible only through a small opening, the transmission of ultrasonic energy from the transducer to the probe tip is maximized by, e.g., using a rigid transmission member to transmit the energy. Accordingly, existing ultrasonic probes, such as the probe marketed under the trademark CUSA® by Valleylabs of Boulder, Colo., are rigid and tapered along their entire length, and have short working lengths.

Unfortunately, because of their rigidity, taper, and short working lengths, existing probes cannot be easily used in conjunction with neuroendoscopes. In other words, existing ultrasonic probes cannot be easily advanced through the small-diameter working lumen of a flexible neuroendoscope, because the rigidity and taper of existing ultrasonic neurosurgery probes prevents them from assuming the variably arcuate shape of the flexible neuroendoscope. Additionally, taper and the short working lengths of existing ultrasonic probes precludes their use in the elongated narrow working channel of a rigid disposable neuroendoscopic sheath.

Flexible ultrasonic probes have been introduced for angioplasty applications to break up blood vessel blockages with precision. It happens that an ultrasonic probe intended for angioplasty applications must be flexible substantially throughout its length, because such a probe typically must be advanced through lengthy tortuous paths in the venous system. As discussed above, however, the desired flexibility of an ultrasonic probe, on the one hand, is a competing characteristic with the desired maximized ultrasonic energy transmission characteristics, on the other hand. Stated differently, a flexible ultrasonic probe does not transmit ultrasonic energy as efficiently as does a rigid probe.

Furthermore, many existing flexible ultrasonic probes do not provide means for aspirating tissue once the tissue has been broken down. As recognized by the present invention, for neurosurgery and endoscopy applications, tissue, once broken down ultrasonically, must then be aspirated from the patient's body through a narrow channel.

Accordingly, it is an object of the present invention to provide an ultrasonic probe which can be used in conjunction with a neuroendoscope, and which maximizes the transmission of amplified ultrasonic energy through the probe. Another object of the present invention is to provide an ultrasonic probe which can be used in conjunction with a neuroendoscope for breaking down tumors, cysts, and hematomas in the nervous system of a patient and then aspirating the broken down tissue. Still another object of the present invention is to provide an ultrasonic probe which can be used in conjunction with a neuroendoscope which is easy to use and cost effective.

SUMMARY OF THE INVENTION

A device for resecting neurological tissue is configured for engaging a lumen of a neurosurgery instrument. Also, the device can be coupled to an ultrasonic transducer that generates ultrasonic vibrations having a wavelength. Per the present invention, the device includes a proximal ultrasonic horn having a distal end and a proximal end couplable to the transducer. An elongated probe is includes which defines a distal tip for transmitting ultrasonic vibrations to the tissue to break down the tissue. Also, a hub is threadably engaged with the horn and is surroundingly engaged with the probe to couple the probe to the horn. To evacuate portions of tissue broken down by the tip, an aspiration channel is juxtaposed with the tip.

Preferably, the probe is hollow, and the probe defines the aspiration channel. In addition, an irrigation channel is established between the lumen of the neurosurgery instrument and the probe. In the preferred embodiment, the probe defines a transverse axis, and the tip is cleaved to establish an oblique angle relative to the transverse axis.

In another aspect, an apparatus is couplable to an ultrasonic transducer for breaking down tissue in the head or spine of the patient when the apparatus is juxtaposed with the tissue and the transducer is activated. As disclosed in detail below, the apparatus includes an elongated neurosurgery instrument having at least one lumen, and an elongated ultrasonic probe is engaged with the at least one lumen of the neurosurgery instrument. The ultrasonic probe includes a distal tip. An aspiration channel is configured for removing portions of the tissue when the aspiration channel is evacuated.

In yet another aspect, a method for resecting tissue in the spine or brain of a patient includes providing an ultrasonic probe that includes a proximal segment and a distal segment terminating in an ultrasonic tip. The method further includes coupling an ultrasonic transducer to the proximal segment of the ultrasonic probe for selectively ultrasonically exciting the ultrasonic tip. Additionally, the method includes establishing an aspiration channel near the ultrasonic tip, and engaging the ultrasonic probe with a lumen of a neurosurgical instrument. The probe is advanced through the lumen until the ultrasonic tip is juxtaposed with the tissue to be resected. Then, the ultrasonic transducer is energized to resect the tissue, and the aspiration channel evacuated.

In a still further aspect, an elongated rigid introducer sheath defines an axis and includes a probe that is parallel to the axis. A handpiece is attached to the probe proximally thereto. Also, a main lumen includes a handpiece segment in the handpiece and a probe segment in the probe. In accordance with the present invention, the handpiece segment defines an angle of between nine degrees and nineteen degrees (9°–19°), and preferably fourteen degrees (14°), with respect to the axis. Preferably, a low-friction coating is deposited in the main lumen.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
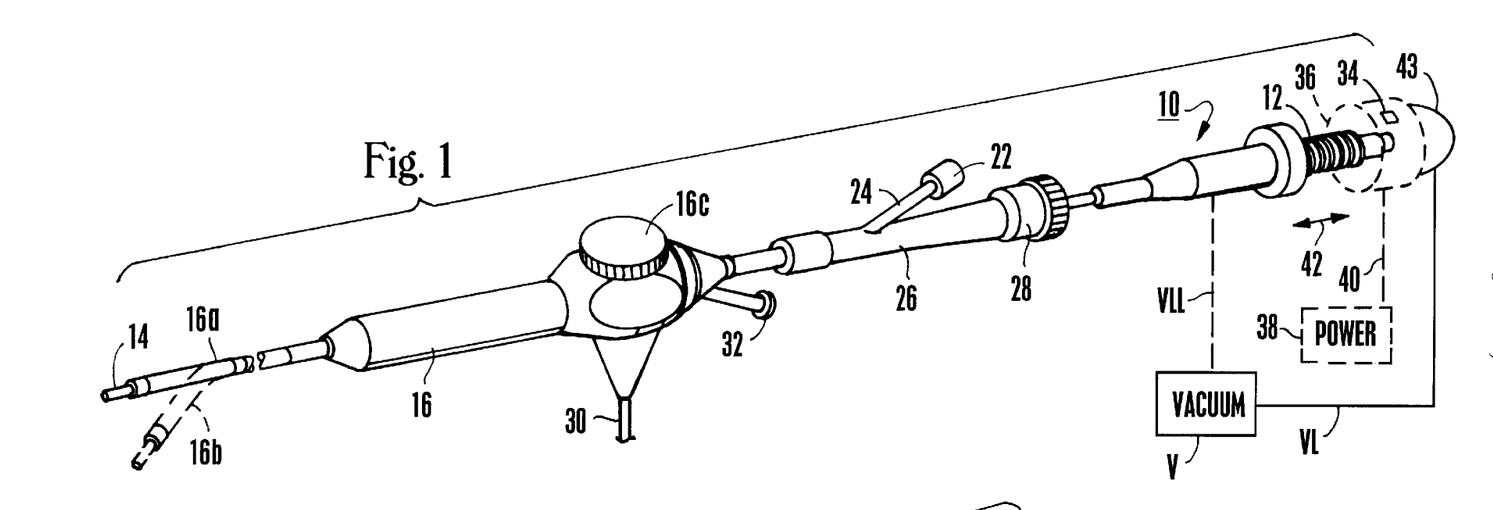
FIG. 1 is a perspective view of the ultrasonic tissue resector of the present invention, shown in operable engagement with the working channel of a flexible neuroendoscope in a straight configuration and showing in phantom the neuroendoscope with flexible distal segment of the ultrasonic tissue resector in a curved configuration.

Referring initially to FIG. 1, a hollow metal ultrasonic tissue resector for resecting tumors, cysts, and hematomas in the brain and spine of a patient and for resecting herniated spinal discs is shown, generally designated 10. As shown, the resector 10 includes a hollow metal horn 12 and a distal tip 14, and the resector 10 is preferably slidably disposed in a working channel of a neuroendoscope 16. Owing to the long working length of the resector 10, the distal tip 14 of the resector 10 protrudes beyond the distal end of the neuroendoscope 16, while the proximal horn 12 of the resector 10 protrudes beyond the proximal end of the neuroendoscope 16.

Once positioned in the neuroendoscope 16, the resector 10 is preferably radially supported in the neuroendoscope 16 by an appropriate fluid seal (not shown in FIG. 1), such as a fluid seal made by Touhy-Borst. In one presently preferred embodiment, the neuroendoscope 16 is a neuroendoscope disclosed in U.S. Pat. No. 5,318,526 or a neuroendoscope disclosed in U.S. patent application Ser. No. 08/535,886, both of which are assigned to the same assignee to which the present invention is assigned, U.S. Pat. No. 5,318,526 incorporated herein by reference.

Accordingly, the neuroendoscope 16 includes a flexible hollow distal tube 16a which is biased to the straight configuration shown. As disclosed in the above-referenced documents, a distal segment 16b of the tube 16a can be selectively moved to a curved configuration, shown in phantom in FIG. 1, by appropriately rotating a control wheel 16c of the neuroscope 16 which causes reciprocating motion of a hypotube-supported activating wire that is connected to the distal segment 16b. Advantageously, the resector 10 includes a flexible distal segment that can assume the shape of the distal segment 16b of the neuroendoscope 16, as discussed below.

A first source 22 of irrigating fluid is in fluid communication with the resector 10 via a first irrigating line 24. In the particular embodiment shown, the irrigating line 24 is connected to a Y-fitting 26 including a Touhy-Borst valve 28. Fluid from the source 22 of irrigating fluid can be directed through the working channel of the neuroendoscope 16 along the outside surface of the resector 10.

Additionally, a bundle 30 of image and illumination optical fibers extend through one of the lumens of the neuroendoscope 16 to illuminate the region beyond the distal end of the scope 16 and to transmit an image of the region to a viewing monitor (not shown), in accordance with endoscopic principles well-known in the art. To facilitate a clear picture from the neuroendoscope of the present invention, fluid from a second fluid source (not shown) can be directed through a scope irrigation channel fitting 32 of the neuroendoscope 16.

FIG. 1 shows that the horn 12 of the resector 10 is externally threaded. In accordance with the present invention, an ultrasonic transducer 34 is mounted in a housing 36, and the horn 12 of the resector 10 is threadably engageable with the housing 36, preferably to a torque of between fifteen inch-pounds to twenty inch-pounds (15 in.lbs.–20 in.lbs.) to couple the resector 10 with the transducer 34. Preferably, the ultrasonic transducer 34 is a piezoelectric crystal which is electrically connected to a source 38 of electrical current via an electrical line 40 as appropriate for energizing the transducer 34 to cause the transducer 34 to mechanically vibrate back-and-forth in the longitudinal dimension, i.e., in the dimension indicated by the arrows 42. In accordance with ultrasonic principles, the ultrasonic transducer 34 vibrates with a frequency, preferably between about eighteen kiloHertz and forty kiloHertz (18 kHz–40 kHz), and the frequency defines a wavelength λ. In other words, the present invention recognizes that for neurosurgery applications, the frequency of vibration is preferably above the audible range. As discussed below, the vibrations are transmitted through a transmitting medium to the target tissue.

It can be appreciated in reference to FIG. I that a source "V" of vacuum is in fluid communication with the lumen of the resector 10 via a vacuum line "VL" and a vacuum fitting 43. The vacuum fitting 43 is preferably formed as part of the housing 36, and is in fluid communication with and coaxial relative to the lumen of the resector 10. Thus, a vacuum lumen extends through the housing 36 to the vacuum line "VL". Alternatively, fluid communication between the source "V" of vacuum and the lumen of the resector 10 can be established via a vacuum line "VLL" (shown in phantom in FIG. 1) and through the horn 12. By appropriately evacuating the lumen of the resector 10, resected tissue can be removed from the patient endoscopically. Also, selected portions of the resector 10 can be cooled thereby, and the fluid pressure and temperature within the patient's skull can be maintained at a predetermined equilibrium value. In the preferred embodiment, the source "V" of vacuum is a peristaltic pump.

Figure 2:
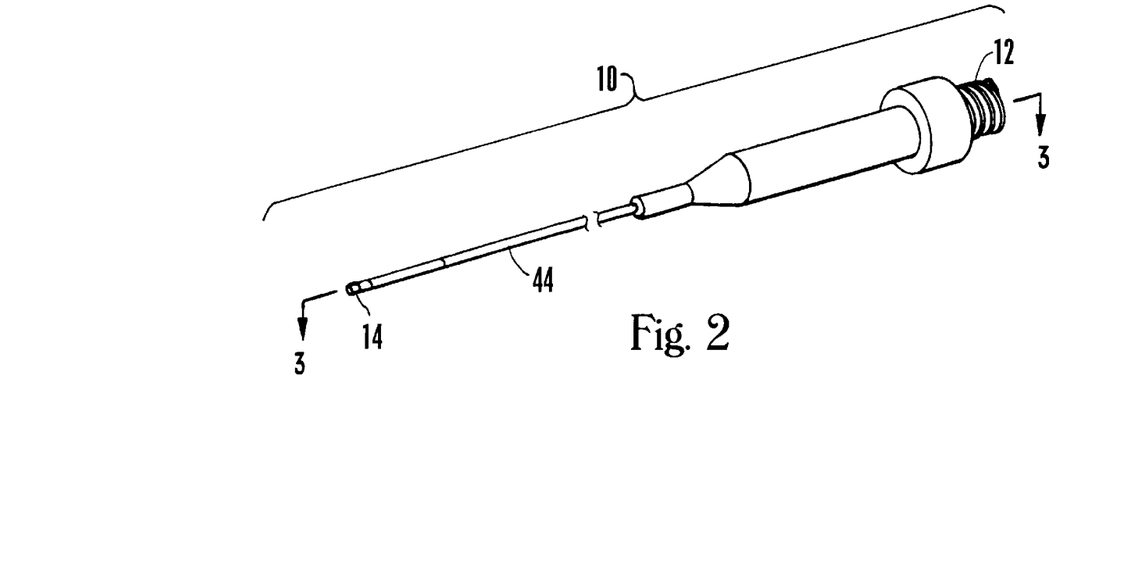
FIG. 2 is a perspective view of the ultrasonic tissue resector, with portions of the ultrasonic probe broken away for clarity.
Figures 3, 3A, 4A, 4B, 4C:
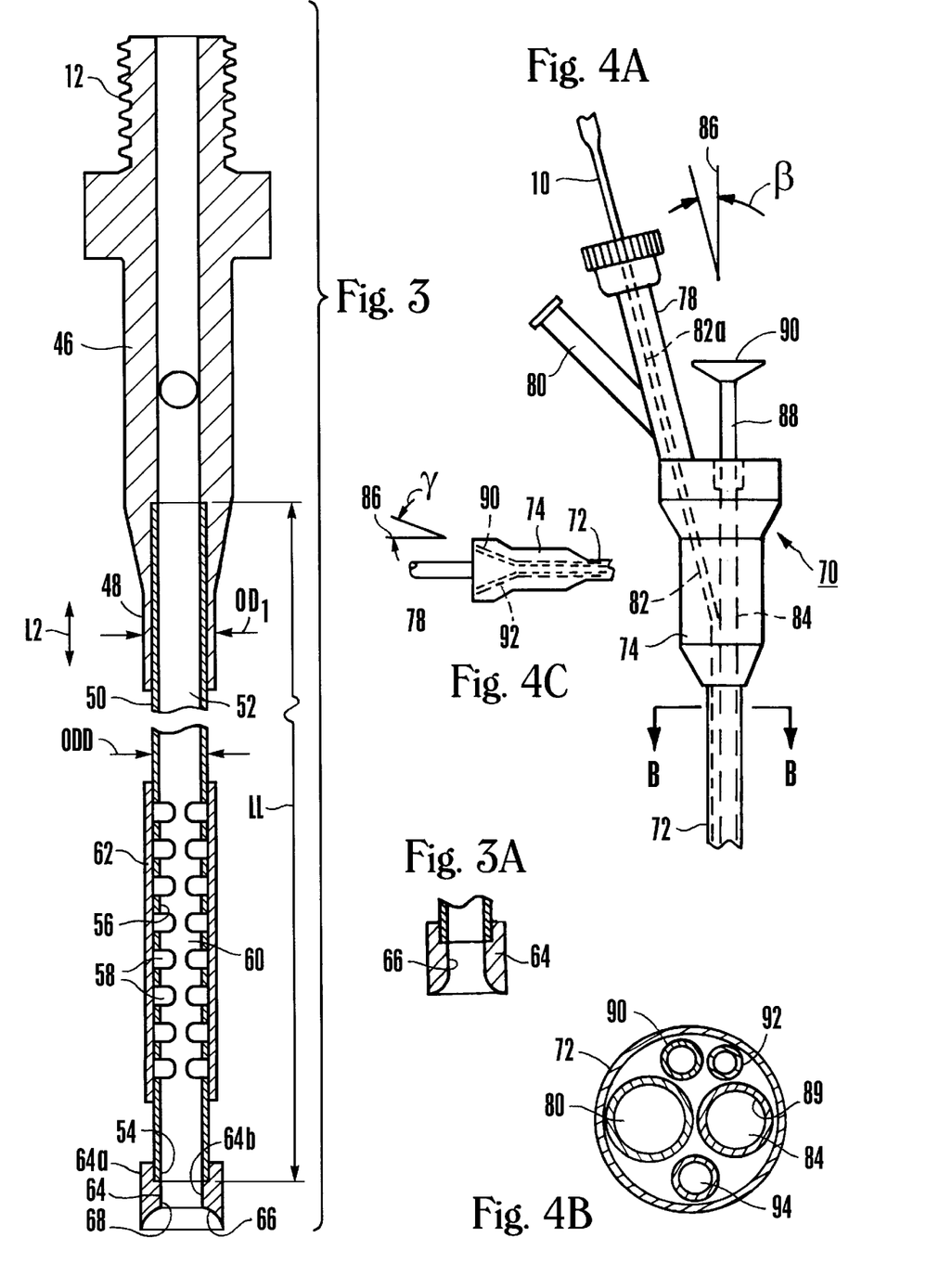
FIG. 3 is a cross-sectional view of the ultrasonic tissue resector as would be seen along the line 3—3 in FIG. 2.
FIG. 3A is a cross-sectional view of an alternate embodiment of the ultrasonic tip.
FIG. 4A is a side view of the ultrasonic tissue resector of the present invention, shown in operable engagement with the working channel of a rigid disposable introducer sheath, with portions broken away and portions shown in phantom.
FIG. 4B is a cross-sectional view as would be seen along the line B—B in FIG. 4A, with the resector and eyepiece removed for clarity.
FIG. 4C is a plan view as would be seen viewing the sheath in FIG. 4A from the bottom, with portions of the offset lumens shown in phantom.

Referring now to FIGS. 2 and 3, the resector 10 includes a hollow metal probe 44 extending distally away from the threaded horn 12. Preferably, the probe 44 is made of a material which optimizes transmission of ultrasonic energy through the probe 44, e.g., Aluminum, stainless steel, Titanium, Nitonol, or an alloy thereof. The probe 44 includes a handle 46 which is distal to the horn 12 and which is formed integrally therewith or connected thereto by means well-known in the art.

As shown best in FIG. 3, the handle 46 tapers distally to a hollow cylindrical proximal transmitting element 48 which, together with the handle 46 and horn 12, establishes a proximal transmitting member. Preferably, the proximal transmitting element 48 defines an outside diameter $OD_1$ of about ninety four thousandths of an inch (0.094"). Also, to further optimize the transmission of ultrasonic energy through the proximal transmitting element 48, the length L2 of the proximal transmitting element 48 is equal to ½n*λ, wherein n is a natural number. Consequently, the proximal transmitting element 48 is relatively rigid when made of the materials mentioned above.

FIG. 3 shows that a hollow cylindrical distal transmitting element 50 is attached to the proximal transmitting element 48 coaxial thereto. Together, the transmitting element 48, 50, handle 46, and horn 12 establish a transmitting member defining a central aspiration channel 52 and terminating in a distal end 54.

In accordance with the embodiment shown in FIGS. 2 and 3, when the transmitting elements 48, 50 are made of materials that are dissimilar to each other such that the elements 48, 50 cannot be welded together, the distal transmitting element 50 is crimped or swaged to the proximal transmitting element 48 to a pull strength of about one hundred pounds (100#). Further, when the elements 48, 50 are made of materials that permit welding the elements 48, 50 together, they are welded together. Alternatively, the distal transmitting element 50 is soldered or brazed to the proximal transmitting element 48. One or both of the transmitting elements 48, 50 can be made of Titanium or Nitonol, and when made of Nitonol, the elements 48, 50 are coated with Nickel prior to soldering to facilitate soldering. As yet a further alternative, the distal transmitting element 50 can be externally threaded, the proximal transmitting element can be internally threaded, and then the elements 48, 50 threadably engaged with each other.

As envisioned by the present invention, the distal transmitting element 50 defines a length "LL" of about ten and thirty five hundredths inches (10.35") and an outer diameter "ODD" of about one hundred sixty five thousandths of an inch (0.165"). Near the distal end 54, the distal transmitting element 50 includes a flexible distal segment 56. In the presently preferred embodiment, the distal segment 56 is rendered sufficiently flexible to conform to the neuroendoscope 16 by virtue of the distal segment 56 being formed with a plurality of, preferably seven, notches 58 that are longitudinally spaced from each other. As shown, each notch 58 extends radially around the distal segment 56, but not completely through the distal segment 56. Consequently, a longitudinally continuous strip 60 of the distal segment 56 is established.

As intended by the presently preferred embodiment, a smooth flexible plastic or Teflon® sheath 62 having a low coefficient of friction is disposed around the distal segment 56, to prevent fluid communication through the notches 58. Thereby, evacuating the entire vacuum channel 52 of the probe 44 is facilitated.

A distal hollow ultrasonic tip 64 is coaxially joined to the distal segment 56 at the distal end 54 thereof by means well-known in the art. As shown, the ultrasonic tip 64 is formed with a cylindrical outer surface 64a. In contrast, the tip 64 is formed with an inner surface 64b which includes a distal inner surface 66 that is longitudinally tapered inwardly toward a cylindrical proximal inner surface 68. Moreover, the distal inner surface 66 is longitudinally curved in accordance with wave focussing principles well-known in the art for focussing ultrasonic energy at a predetermined distance distal to the ultrasonic tip 64.

As shown in FIG. 3, the curvature of the distal inner surface 66 can be concave. Alternatively, as shown in FIG. 3A, the curvature of the distal inner surface 66 can be convex. In either case, it is to be understood that the curvature of the distal inner surface 66 is established as appropriate for focussing the ultrasonic energy transmitted by the probe 44 at a predetermined distance from the tip 64.

In the operation of the resector 10 shown in FIGS. 1–3, the resector 10 is slidably engaged with the working channel of the neuroendoscope 16 as shown in FIG. 1. Then, the neuroendoscope 16 is positioned through, e.g., an entry hole in the skull of a patient. Next, the distal segment of the neuroendoscope 16 is bent as desired to juxtapose the tip 14 of the resector 10 with tissue, e.g., a tumor, that is sought to be resected.

Once the resector 10 has been properly positioned, the ultrasonic transducer 30 is energized to cause the transducer 30 to vibrate. The ultrasonic energy is transmitted through the ultrasonic probe of the present invention to ultrasonically excite the tip 14 and cause cavitation nearby the tissue, thereby breaking down the tissue. Also, the source "V" of vacuum is activated to evacuate the aspiration channel 40 and remove broken down portions of tissue from the operating site. The operating site can be irrigated by directing irrigating fluid from the source 22 of irrigating fluid through the irrigation channel 56.

Referring now to FIGS. 4A–4C, the resector 10 can be engaged with a lumen of a rigid elongated neuroendoscopic disposable sheath, generally designated 70. In one presently preferred embodiment, the sheath 70 is a four-lumen rigid steel sheath made by Neuro Navigational Corp. of Costa Mesa, Calif.

As shown in FIG. 4A, the sheath 70 includes a rigid elongated probe 72 proximally coupled to a metal or plastic handpiece 74. A Y-fitting 76 is threadably engaged with or bonded to the handpiece 74. Preferably, the Y-fitting 76 is a Touhy-Borst fitting that includes a hollow main branch 78 and a hollow ancillary branch 80.

The main branch 78 defines a main lumen 82 which joins the lumen of the ancillary branch 80, and the resector 10 is advanced through the main lumen 82. A source of irrigating fluid can be connected to the ancillary lumen 80 to irrigate around the resector 10.

Also, an eyepiece lumen 84 extends through the handpiece 74 and probe 72. The eyepiece lumen 84 is parallel to and laterally offset from the axis 86 of the sheath 70. A rigid viewing scope 88 having an eyepiece 90 is advanceable through the eyepiece lumen 84.

As shown best in FIG. 4A, the main branch 78 (and, hence, a handpiece segment 82a of the main lumen 82 therein) establishes an angle β with respect to the axis 84 of the sheath 70. In the presently preferred embodiment, the angle β is between about nine degrees and nineteen degrees (9°–19°), and more preferably is about fourteen degrees (14°). The main lumen 78 is bent as shown within the handpiece 74 such that it extends through the probe 82 parallel to the axis 86 of the sheath 70.

We have found that by establishing the angle β as described, interference between the resector 10 and the scope 88 is avoided, while at the same time undue friction between the resector 10 and main lumen 82 (which friction tends to increase with higher values of the angle β, i.e., angle in excess of 20°) is avoided during operation of the resector 10. As envisioned by the present invention, because friction between the resector 10 and main lumen 82 degrades the effectiveness of the resector 10 (and unduly heats the main lumen 82), it is advantageous to reduce friction even further by depositing a low-friction coating 89 (FIG. 4B), preferably made of TFE Teflon®, on the cylindrical wall of the main lumen 82.

FIGS. 4B and 4C show that in addition to the main lumen 80 and eyepiece lumen 84, both of which extend through the probe 72 to the distal end thereof, additional lumens are formed in the sheath 70. More specifically, two opposed offset lumens 90, 92 are formed in the handpiece 74. In the handpiece 74, the offset lumens 90, 92 each establish an offset angle y with respect to the axis 86 of the sheath 70, to avoid interference between the components attached to the offset lumens 90, 92 and the other components attached to the sheath 70 described above. In the preferred embodiment, the offset angle γ is equal to about fifteen degrees (15°). Like the main lumen 82, the offset lumens 90, 92 are bent within the handpiece 74 such that they extend through the probe 82 parallel to the axis 86 of the sheath 70. Furthermore, a fifth lumen 94 can be established in the sheath 70, as best shown in FIG. 4B. It is to be understood that the offset and fifth lumens 90, 92, 94 can be used as irrigation lumens, evacuation lumens, working channel lumens, or fiber optic lumens as desired.

Figure 5:
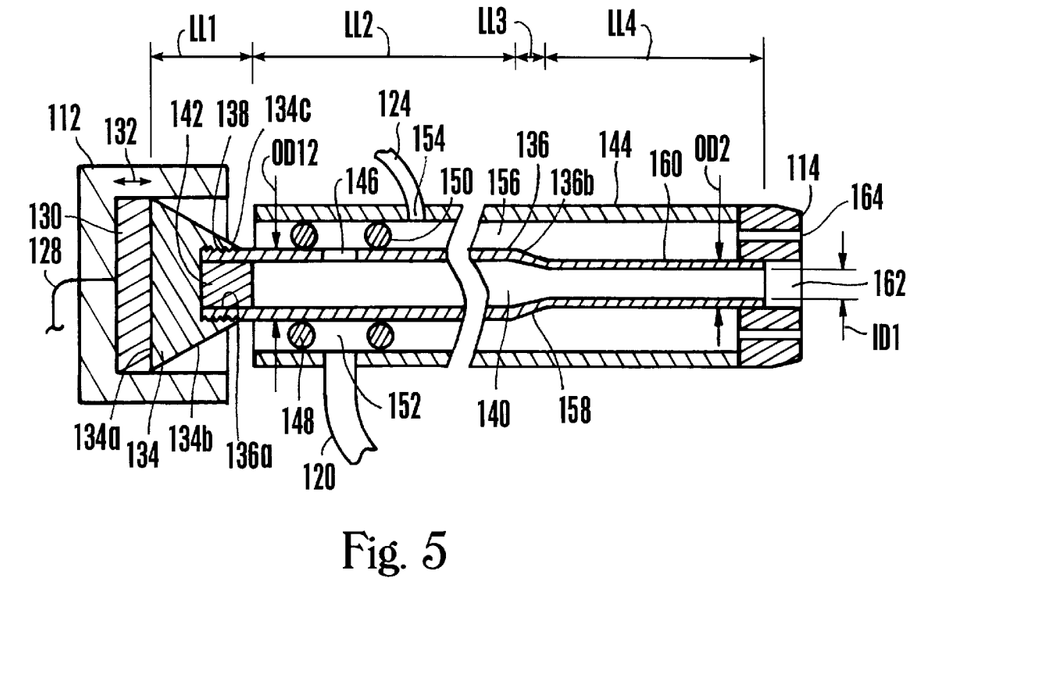
FIG. 5 is a cross-sectional view of an alternate embodiment of the ultrasonic tissue resector as would be seen along the line 3—3 in FIG. 2, with the neuroendoscope removed for clarity, the flexible distal segment of the ultrasonic tissue resector in a straight configuration, and portions of the ultrasonic probe broken away for clarity.

Now referring to FIG. 5, in an alternate embodiment an ultrasonic transducer 130 can be operably engaged with an ultrasonic probe including a rigid primary ultrasonic taper 134 having a proximal end 134a that is mechanically coupled to the ultrasonic transducer 130 by means well-known in the art. In the preferred embodiment, the primary ultrasonic taper 134 is a so-called horn having a distally tapered portion 134b, the contour of which is a taper such as is defined by a Gaussian or exponential function or linear taper, in accordance with principles well-known in the art.

As the skilled artisan will recognize, the primary ultrasonic taper 134 amplifies longitudinal displacements, i.e., longitudinal vibrations, that are caused by the ultrasonic transducer 130 and transmits the displacements from the proximal end 134a of the primary taper 134 to a distal end 134c of the primary taper 134. To optimize the transmission of ultrasonic energy, the primary taper 134 has an effective length LL1 that bears a predetermined relationship to the wavelength λ. In one embodiment, LL1 is equal to ½n*λ, wherein n is a natural number. In another embodiment, LL1 is equal to 0.25n*λ, wherein n is an odd number. As intended by the present invention, the above-described combination of structure ensures that vibration amplitude loss is minimized by ensuring that junctions between components of the device shown are positioned at ultrasonic nodes.

A rigid, tubular, hollow ultrasonic transmitting member 136 has a proximal end segment 136a that is connected to the distal end 134c of the primary ultrasonic taper 134. The transmitting member 136 is made of a material which optimizes transmission of ultrasonic energy through the member 136, e.g., Aluminum, Titanium, Nitonol, or an alloy thereof, and the member 136 defines an outside diameter $OD_{11}$ of about ninety four thousandths of an inch (0.094"), such that the transmitting member 136 is relatively rigid when made of the materials mentioned above. Also, to further optimize the transmission of ultrasonic energy through the transmitting member 136, the length LL2 of the member 136 is equal to ½n*λ, wherein n is a natural number.

Preferably, to permit reuse, the ultrasonic transmitting member 136 is detachably coupled to the primary ultrasonic taper 134. To this end, in the embodiment shown the proximal end segment 136a of the ultrasonic transmitting member 136 is threaded for detachably engaging a complementarily configured recess 138 which is formed in the primary ultrasonic taper 134. Alternative structure may be used for detachably coupling the ultrasonic transmitting member 136 to the primary ultrasonic taper 134, e.g, a detent may be formed on one of the transmitting member 136 and primary ultrasonic taper 134, and a complementary cavity formed on the other component to receive the detent.

As can be appreciated in reference to FIG. 5, the hollow transmitting member 136 defines an aspiration channel 140. Further, a plug 142 is positioned in aspiration channel 140 in the proximal end segment 136a of the ultrasonic transmitting member 136 to block the aspiration channel 140.

FIG. 5 additionally shows that a flexible hollow catheter 144 surrounds and is closely spaced from the ultrasonic transmitting member 136. An aspiration port 146 is formed in the ultrasonic transmitting member 136, and proximal and distal fluid seals 148, 150 are positioned between the catheter 144 and the ultrasonic transmitting member 136. Preferably, the fluid seals 148, 150 are resilient toroidal-shaped rubber or plastic o-rings which establish a ring-shaped aspiration plenum 152 between the catheter 144 and the ultrasonic transmitting member 136. As shown, the aspiration plenum 152 communicates with a vacuum line 120 and, hence, with a source 118 of vacuum. Consequently, it may now be appreciated that the source 118 of vacuum can be activated to evacuate the aspiration channel 140.

Furthermore, an irrigation port 154 is formed in the catheter 144 distal to the distal fluid seal 150. An irrigation channel 156 is established between the catheter 144 and the ultrasonic transmitting member 136 distal to the distal fluid seal 150, and the irrigation channel 156 communicates with a source of irrigating fluid via the irrigation port 154 and irrigating line 124. As mentioned above, the irrigating fluid cools selected energized components, for example, the transmitting member 136, particularly where the transmitting member 136 might rub against, e.g., a bond in the neuroendoscope 16. Further, the irrigating fluid can be directed through the irrigating channel 156 to maintain intercranial pressure at a predetermined equilibrium value, ordinarily a value within normal physiological limits. Moreover, the irrigating fluid establishes a medium for ultrasonic vibration and the cavitation induced by the ultrasonic vibration.

Continuing with the description of FIG. 5, the ultrasonic transmitting member 136 has a distal end 136b which terminates in a rigid hollow secondary ultrasonic taper 158. Preferably, the secondary ultrasonic taper 158 is a horn having a length LL3 equal to $\frac{1}{2}n^*\lambda$, wherein n is a natural number.

In turn, the secondary ultrasonic taper 158 terminates at its distal end in a hollow tubular flexible joining member 160 having a length LL4 equal to $0.25n^*\lambda$, wherein n is an odd integer. Thus, in the preferred embodiment the ultrasonic transmitting member 136, secondary ultrasonic taper 158, and flexible joining member 160 are formed integrally together, i.e., as a unitarily-formed structure. In other words, the ultrasonic components of the present invention each and collectively bear a predetermined relationship to the wavelength $\lambda$.

As intended by the present invention, the flexible joining member 160 is flexible owing to its small diameter, relative to the diameter of the transmitting member 136. More particularly, the inside diameter ID of the flexible joining member 160 is equal to about twenty thousandths of an inch (0.020"), and the outside diameter $OD_{21}$, of the flexible joining member 160 is equal to about thirty thousandths of an inch (0.030").

Consequently, when the flexible joining member 160 and transmitting member 136 are made of the materials mentioned above and configured as disclosed, the joining member 160 is relatively flexible compared to the transmitting member 136. By relatively flexible is meant that the flexible joining member 160 can assume the shape of the bendable distal segment of the neuroendoscope 16 shown in FIG. 1, when the neuroendoscope 16 is operated as disclosed in the above-referenced U.S. Patent and patent application.

Alternatively, instead of being a tubular structure throughout its entire length, it is to be understood that as intended by the present invention, the flexible joining member 160 can be established by a diametrically attenuated distal portion 158a of the secondary ultrasonic taper 158. This might be the case in applications wherein, because of the design of the secondary taper 158, its distal portion 158a is sufficiently long and flexible so as to allow the distal portion to assume the shape of the distal end of the neuroendoscope 16. Consequently, in such a case, the flexible joining member 160 is not a structure in addition to the secondary taper 158, but rather is established by the secondary taper 158.

In either case, the present invention recognizes that in contrast to angioplasty applications, an ultrasonic probe intended for neurosurgery need not be flexible throughout its entire length, but only for the distal most segment of the probe. This is because neuroendoscopes (and accompanying surgical instruments, such as ultrasonic probes) are typically advanced only a few centimeters into a patient.

A tip 114 is included which is a rigid structure that is fixedly connected to the flexible joining member 160 for transmitting ultrasonic energy to tissue to break down the tissue. e.g., by cavitation or by direct impact, More particularly, the tip 114 is formed with a central channel 162, and the flexible joining member 160 is positioned in the central channel 162 and is bonded to the tip 114 to transmit ultrasonic energy to the tip 114. Together, the tip 114, flexible joining member 160, secondary taper 158, and transmitting member 136 establish an ultrasonic probe, and the ultrasonic probe of the present invention consequently includes a rigid proximal segment that is defined in part by the transmitting member 136 and a flexible distal segment that is defined by the flexible joining member 160.

As shown, the central channel 162 of the tip 114 communicates with the aspiration channel 140. Consequently, a source of vacuum can be activated to aspirate, through the central channel 162, tissue that is broken down by the tip 114. Stated differently, the aspiration channel 140 is juxtaposed with the tip 114 for evacuating portions of tissue broken down by the tip 114.

Furthermore, a ring-shaped irrigation outlet port 164 is formed in the tip 114. The irrigation outlet port 164 communicates with the irrigation channel 156, such that fluid from a source of irrigating fluid can be flushed through the irrigation outlet port 164 to irrigate the surgery site.

Figure 6:
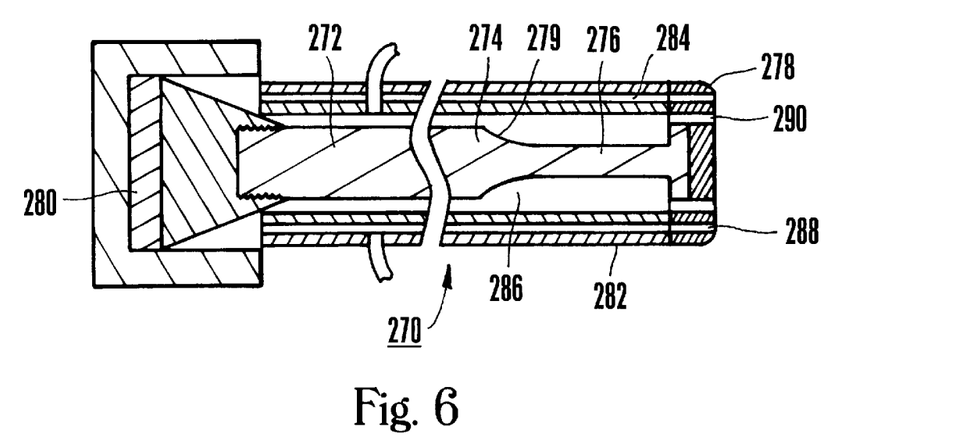
FIG. 6 is a cross-sectional view of yet another alternate embodiment of the ultrasonic tissue resector as would be seen along the line 3—3 in FIG. 2, with the neuroendoscope removed for clarity, the flexible distal segment of the ultrasonic tissue resector in a straight configuration, and portions of the ultrasonic probe broken away for clarity.

FIG. 6 shows another alternate embodiment of the resector of the present invention, generally designated 270. The resector 270 shown in FIG. 6 is in all essential respects identical in operation and construction to the resector shown in FIG. 5, with the following exceptions. The resector 270 shown in FIG. 6 includes a solid ultrasonic probe 272 that includes a rigid transmitting member 274 and a flexible joining member 276, which can include a distally flexible taper 279. The joining member 276 connects a tip 278 to the transmitting member 274 for transmitting ultrasonic energy from an ultrasonic transducer 280 to the tip 278.

As shown in FIG. 6, a multi-lumen catheter 282 establishes an irrigation channel 284 and an aspiration channel 286, and the tip 278 is formed with an irrigation outlet port 288 and an aspiration inlet port 290 that respectively communicate with the channels 284, 286. In the embodiment shown in FIG. 6, the lumens of the catheter 282 are concentric, but it is to be understood that the lumens may extend through the catheter longitudinally side-by-side, instead of concentrically.

Figure 7:
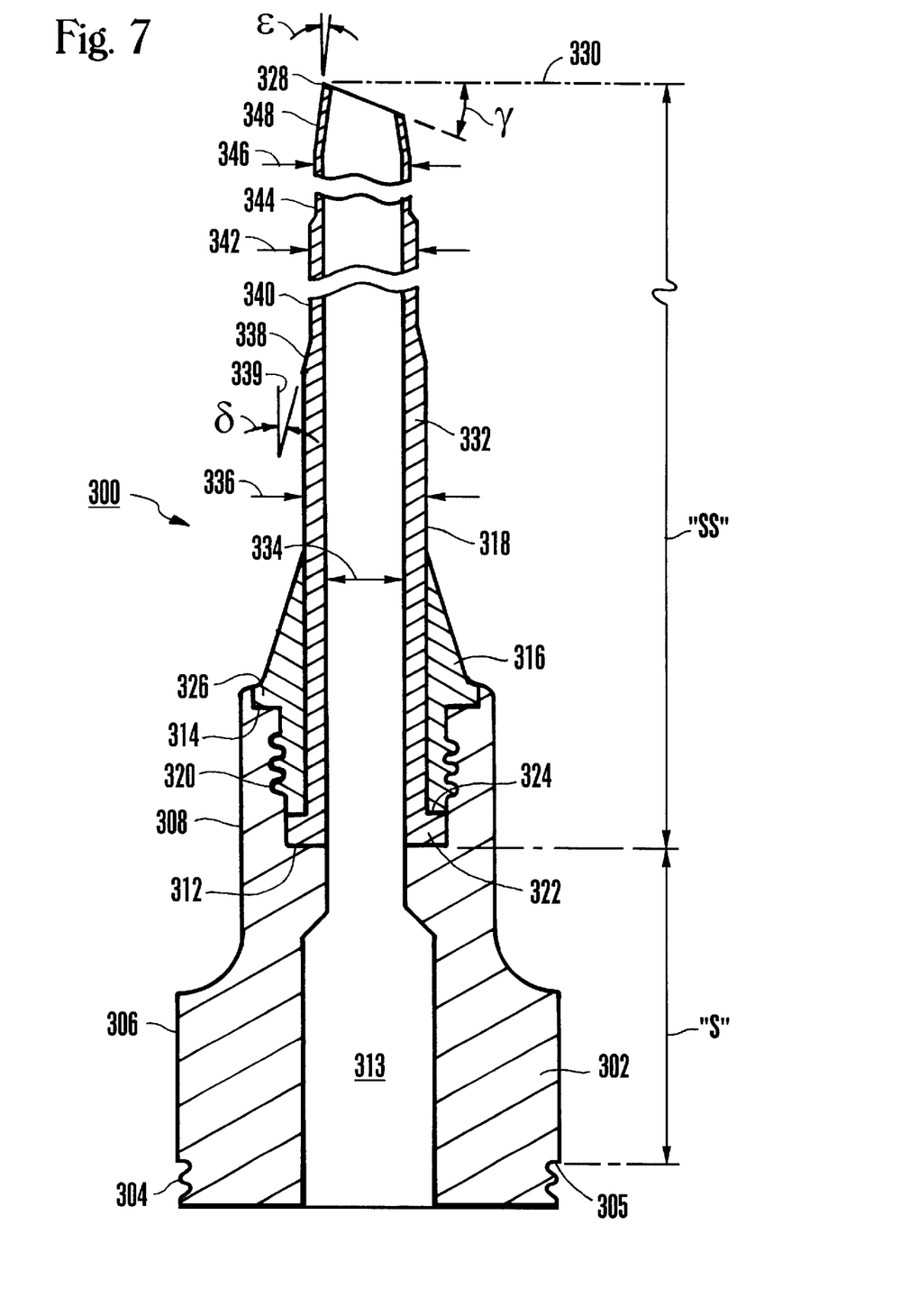
FIG. 7 is a cross-sectional view of still another alternate embodiment of the ultrasonic tissue resector as would be seen along the line 3—3 in FIG. 2.

FIG. 7 shows yet another embodiment of the resector of the present invention, generally designated 300. As shown, the resector 300 includes a rigid metal, preferably aluminum or titanium alloy ultrasonic horn 302 that is formed with an externally threaded proximal segment 304 defining a lip 305. The proximal segment 304 threadably engages the housing 36 (FIG. 1), and is preferably tightened in the housing 36 to a torque of between fifteen inch-pounds to twenty inch-pounds (15 in.lbs.–20 in.lbs.).

As shown in FIG. 7, the horn 302 preferably is a high gain, so-called "step" horn. Thus, in accordance with horn principles known in the art the horn 12 is formed with a radially enlarged portion 306 that tapers distally to a radially smaller portion 308, for amplifying the transmission of ultrasonic energy therealong. As intended by the present invention, the probe 300 defines a vacuum channel 310 that includes a radially expanded portion 312 in the radially enlarged portion 306 of the horn 302.

FIG. 7 shows that the radially smaller portion 308 of the horn 302 is formed with an annular abutment surface 312.

Per ultrasonic transmission principles, the distance "S" between the lip 305 and the abutment surface 312 is one-quarter of a wavelength of the ultrasonic energy.

Distal to the abutment surface 312, the radially smaller portion 308 of the horn 302 is internally threaded as shown. An annular hub surface 314 circumscribes the vacuum channel 310 distal to the internally threaded portion of the horn 302.

In accordance with the present invention, a hollow titanium hub 316 holds a hollow elongated titanium probe 318 tightly against the horn 302 in a mutually coaxial relationship therewith. In the preferred embodiment, the hub 316 is formed with external threads 320 that engage the internally threaded portion of the horn 302. The probe 318 is formed with a proximal disc-shaped collar 322, and the collar 322 is held in tight compression between the abutment surface 312 of the horn 302 and a proximal end 324 of the hub 316. To effect compression of the collar 322 and thereby promote the transmission of ultrasonic energy through the resector 300, the hub 316 is tightened in the horn 302 to a torque of between three inch-pounds and six inch-pounds (3 in.-lbs.–6 in.-lbs.)

Distal to its threads 320, the hub 316 is formed with an annular seating flange 326. As shown, the seating flange 326 is configured for abutting the hub surface 314 and for being closely received in the cavity established by the hub surface 314. Per the embodiment shown in FIG. 7, the outer surface of the hub 316 tapers distally inwardly from the seating flange 326 to the probe 318.

With particular regard to the probe 318, the probe 318 defines a distal tip 328 and a transverse axis 330. As shown in FIG. 7, the distal tip 328 is cleaved in that it establishes an oblique angle $\lambda$, preferably ten degrees to fifteen degrees (10°–15°), with respect to the transverse axis 330, for maintaining a constant vacuum on tissue distal to the tip 328 and for promoting the transmission of energy toward tissue distal to the tip 328. Additionally, the distance "SS" between the lip 305 of the horn 302 and the distal tip 328 of the probe 318 is an integer multiple of one-half the wavelength of the ultrasonic energy being transmitted.

With further regard to the probe 318, the structure of the probe 318 from the collar 322 distal toward the tip 328 can be appreciated in reference to FIG. 7. A hollow proximal segment 332 of the probe 318 extends distally away from the collar 322. The proximal segment 332 defines an inside diameter 334 of about fifty three thousandths of an inch (0.053") and an outside diameter 336 of about one thousand fifty eight ten thousandths of an inch (0.1058").

FIG. 7 shows that the proximal segment 332 of the probe 318 terminates in a distally tapered segment 338. Per the present invention, the taper angle $\delta$ of the tapered segment 338 is about six degrees (6°) relative to the long axis 339 of the probe 318. In turn, the tapered segment 338 terminates in a distally intermediate segment 340 having an outside diameter 342 of about ninety three thousandths of an inch (0.093").

Proceeding with the description of the probe 318, the probe 318 is stepped in that the distally intermediate segment 340 abruptly steps to a distal segment 344 having an outside diameter 346 of about eighty thousandths of an inch (0.080"). The distal segment 344 terminates in a tip segment 348. As shown, the wall of the tip segment 348 is swaged inwardly, such that both the inside and outside diameters of the tip segment 348 taper radially inwardly toward the distal tip 328. In one preferred embodiment, the taper angle $\epsilon$ of the tip segment 348 is between three degrees and ten degrees (3°–10°) relative to the long axis of the probe 318.

While the tip segment 348 has an inwardly tapering inside diameter, it readily can be appreciated in reference to FIG. 7 that the inside diameters of all four segments 332, 338, 340, and 344 are constant and are equal to each other. Stated differently, all four segments 332, 338, 340, and 344 have the same inside diameter. Accordingly, it may now be appreciated that the probe 318 is made from a unitary tube, with the segments 332, 338, 340, and 344 of the probe 318 being established by machining the outer surface of the tube as appropriate. It is further to be appreciated that the lengths of the segments 332, 338, 340, and 344 are established per principles discussed above to optimize the transmission of ultrasonic energy through the probe 318. It is still further to be appreciated that the tapers and steps of the probe 318 disclosed above amplify ultrasonic energy. And, the above-described combination of structure ensures that vibration amplitude loss is minimized by ensuring that junctions between components of the device shown are positioned at ultrasonic nodes.

While the particular ULTRASONIC TISSUE RESECTOR FOR NEUROSURGERY as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A device for resecting neurological tissue, the device being configured for engaging a lumen of a neurosurgery instrument, the device being couplable to an ultrasonic transducer that generates ultrasonic vibrations having a wavelength, the device comprising:

a proximal ultrasonic horn having a distal end and a proximal end couplable to the transducer;

an elongated probe defining a distal tip segment for transmitting ultrasonic vibrations to a tissue to break down a tissue, the probe also defining plural non-tip segments proximal to the distal tip segment, each non-tip segment having the same inside diameter as the other non-tip segments, each non-tip segment having an outside diameter greater than its immediately distal non-tip segment;

a hub threadably engaged with the horn and surroundingly engaged with the probe to couple the probe to the horn; and an aspiration channel juxtaposed with the tip for evacuating portions of tissue broken down by the tip.

2. The device of claim 1, in combination with the neurosurgery instrument.

3. The device of claim 1, wherein the probe is hollow and defines an aspiration channel.

4. The device of claim 3, wherein an irrigation channel is established between the lumen of the neurosurgery instrument and the probe.

5. The device of claim 2, wherein the neurosurgery instrument includes a selectively bendable distal segment.

6. The device of claim 2, wherein the neurosurgery instrument is substantially rigid throughout its length.

7. The device of claim 6, wherein the neurosurgery instrument includes four lumens.

8. The device of claim 1, wherein the probe defines a transverse axis, and the tip establishes an oblique angle relative to the transverse axis.

* * * * *